(12) United States Patent
Tsai et al.

(10) Patent No.: US 10,835,444 B2
(45) Date of Patent: Nov. 17, 2020

(54) SHOE ASSEMBLY FOR A WALKING ASSIST DEVICE

(71) Applicant: FREE BIONICS TAIWAN INC., Hsinchu (TW)

(72) Inventors: Yi-Jeng Tsai, Taoyuan (TW); Ming-Chang Teng, Hsinchu (TW)

(73) Assignee: FREE BIONICS TAIWAN INC., Hsinchu (TW)

( * ) Notice: Subject to any disclaimer, the term of this patent is extended or adjusted under 35 U.S.C. 154(b) by 345 days.

(21) Appl. No.: 15/811,137

(22) Filed: Nov. 13, 2017

(65) Prior Publication Data
US 2018/0200134 A1      Jul. 19, 2018

Related U.S. Application Data

(60) Provisional application No. 62/445,940, filed on Jan. 13, 2017.

(51) Int. Cl.
*A61H 3/00* (2006.01)
*A61H 1/02* (2006.01)
(Continued)

(52) U.S. Cl.
CPC ............... *A61H 3/00* (2013.01); *A61F 2/70* (2013.01); *A61H 1/0262* (2013.01);
(Continued)

(58) Field of Classification Search
CPC ............... A61F 2/50; A61F 2002/5001; A61F 2002/5003; A61F 2/66–2002/6692;
(Continued)

(56) References Cited

U.S. PATENT DOCUMENTS 3,827,430 A * 8/1974 Fadden ................ A61F 5/0113
602/28
7,628,766 B1 * 12/2009 Kazerooni ............... A61F 5/00
602/16
(Continued)

FOREIGN PATENT DOCUMENTS

CN      103610568 A      3/2014
CN      103860357        6/2014
(Continued)

OTHER PUBLICATIONS

Office Action from JPO dated Mar. 13, 2019 for related JP application 2018-077510.
(Continued)

*Primary Examiner* — Alvin J Stewart
(74) *Attorney, Agent, or Firm* — WPAT, P.C., Intellectual Property Attorneys; Anthony King

(57) ABSTRACT

The present invention discloses a shoe assembly for a walking assist device. The shoe assembly includes a shoe pad, and a shoe cover on the shoe pad. The shoe cover includes a recessed portion to accommodate a first portion of a side plate connected between the shoe cover and a shank stand of the walking assist device, and includes a support plate on the shoe pad to fulcrum a second portion of the side plate. The second portion covers the recessed portion while the first portion is held in the recessed portion.

20 Claims, 15 Drawing Sheets

(51) Int. Cl.
*A61F 2/70* (2006.01)
*B25J 9/00* (2006.01)

(52) U.S. Cl.
CPC .......... *A61H 1/0266* (2013.01); *B25J 9/0006* (2013.01); *A61H 2201/0192* (2013.01); *A61H 2201/1207* (2013.01); *A61H 2201/164* (2013.01); *A61H 2201/165* (2013.01); *A61H 2201/1671* (2013.01); *A61H 2201/1676* (2013.01); *A61H 2205/12* (2013.01)

(58) Field of Classification Search
CPC .... A61H 3/00; A61H 2003/007; A61H 3/008; A61H 1/0237; A61H 1/0266; B25J 9/0006
See application file for complete search history.

(56) References Cited

U.S. PATENT DOCUMENTS

| | | | | |
|---|---|---|---|---|
| 8,070,700 B2* | 12/2011 | Kazerooni | ................ | A61F 5/00 602/16 |
| 9,333,644 B2* | 5/2016 | Angold | .................... | B66D 3/18 |
| 9,526,668 B2* | 12/2016 | Goffer | .................... | B25J 9/0006 |
| 9,687,409 B2* | 6/2017 | Teng | ....................... | A61H 1/024 |
| 10,124,484 B1* | 11/2018 | Barnes | .................... | B25J 9/0006 |
| 10,179,079 B2* | 1/2019 | Strausser | .................. | A61H 3/00 |
| 10,548,800 B1* | 2/2020 | Barnes | ................. | A61H 1/0262 |
| 2002/0013628 A1* | 1/2002 | Harris | ....................... | A61F 2/66 623/55 |
| 2002/0183860 A1* | 12/2002 | Wilkinson | ................ | A61F 2/66 623/52 |
| 2007/0056592 A1* | 3/2007 | Angold | .................... | A61H 3/00 128/845 |
| 2010/0069804 A1* | 3/2010 | Linares | .................... | A61H 3/00 602/16 |
| 2010/0076360 A1* | 3/2010 | Shimada | ............... | A61F 5/0102 602/23 |
| 2010/0094188 A1* | 4/2010 | Goffer | .................. | A61H 1/0266 602/23 |
| 2011/0320012 A1* | 12/2011 | Christensen | .......... | A61F 2/6607 623/55 |
| 2012/0130508 A1* | 5/2012 | Harris | .................... | A61F 2/6607 623/50 |
| 2013/0102934 A1* | 4/2013 | Ikeuchi | ................ | A61H 1/0244 601/35 |
| 2013/0267878 A1* | 10/2013 | Franke | .................... | A61F 2/602 602/7 |
| 2014/0100493 A1* | 4/2014 | Craig | ........................ | A61H 3/00 601/35 |
| 2014/0276265 A1* | 9/2014 | Caires | .................. | A61H 1/0266 601/34 |
| 2015/0025423 A1* | 1/2015 | Caires | ...................... | A61H 3/00 601/35 |
| 2017/0273852 A1* | 9/2017 | Nakashima | ...... | A63B 21/00181 |
| 2018/0104075 A1* | 4/2018 | Mooney | ..................... | A61F 5/01 |
| 2018/0125679 A1* | 5/2018 | Kaltenborn | ............... | A61F 2/66 |
| 2018/0289578 A1* | 10/2018 | Suzuki | ................. | A61H 1/0262 |
| 2019/0201274 A1* | 7/2019 | Teng | ........................ | A61H 3/00 |
| 2019/0282424 A1* | 9/2019 | Lerner | ..................... | A61H 3/00 |

FOREIGN PATENT DOCUMENTS

| | | |
|---|---|---|
| CN | 106821684 A | 6/2017 |
| CN | 107049713 A | 8/2017 |
| CN | 107106399 A | 8/2017 |
| EP | 2923685 A | 9/2015 |
| JP | 1995-29891 A | 6/1995 |
| JP | 2010125030 A | 6/2010 |
| JP | 2011-110176 A | 6/2011 |
| JP | 2013-173190 A | 9/2013 |
| JP | 2017-94427 A | 6/2017 |
| KR | 101025512 | 12/2010 |
| TW | 201436780 A | 10/2014 |
| WO | 2015019485 | 2/2015 |

OTHER PUBLICATIONS

Office Action from JPO dated Oct. 9, 2019 for related JP application 2018-077513.
EPO search report and provisional opinion dated Jan. 17, 2019 for related EP application 18178307.
EPO search report dated Jan. 9, 2019 for related EP application 18178308.
Office Action from JPO dated Mar. 13, 2019 for related JP application 2018-077513.
Office Action dated Aug. 12, 2020 issued by China National Intellectual Property Office for counterpart application No. 201810264294.7.
Search Report dated Aug. 12, 2020 issued by China National Intellectual Property Office for counterpart application No. 201810264294.7.

* cited by examiner

SHOE ASSEMBLY FOR A WALKING ASSIST DEVICE

CROSS REFERENCE TO RELATED APPLICATIONS

This application claims priority to U.S. provisional application Ser. No. 62/445,940, filed 13 Jan. 2017, which is incorporated herein by reference in its entirety.

BACKGROUND

A walking assist device, also known as exoskeleton robot, is a wearable mobile machine that supports the body of a user and move limbs of the user. Generally, a walking assist device is powered by a system of electric motors, pneumatics, levers, hydraulics, or a combination of technologies that can move limbs. One of the main applications is medical. A walking assist device can help persons who lose or lose control of their legs or arms due to illness or accidental injury. While the walking assist device is worn by a user, security issue may arise. For example, the user may not keep a poised posture during walking, and may tend to significantly sway to the right when supported with the right leg and sway to the left when supported with the left leg. Such sway is likely to cause a linear contact and not a safe surface contact between a shoe assembly of the walking assist device and the ground. Consequently, the user may trip or fall on the ground.

It may therefore be desirable to have a shoe assembly that ensures a stable contact with the ground for a user of the walking assist device during walking.

SUMMARY

The present invention is directed to a shoe assembly for a walking assist device, and a walking assist device comprising the shoe assembly.

Embodiments according to the present invention provide a shoe assembly for a walking assist device. The shoe assembly includes a shoe pad, and a shoe cover. The shoe cover includes a recessed portion to accommodate a first portion of a side plate connected between the shoe cover and a shank stand of the walking assist device, and a support plate on the shoe pad to fulcrum a second portion of the side plate. The second portion covers the recessed portion while the first portion is held in the recessed portion.

In an embodiment, the shank stand extends in a first direction, and the first portion and the second portion of the side plate extend in a second direction different from the first direction.

In another embodiment, the second portion is elastically deformed in response to a force exerted along the first direction.

In yet another embodiment, the support plate includes a raised surface to fulcrum the second portion, and a slope having an inclined surface to receive the second portion when elastically deformed.

In yet another embodiment, the support plate having a height that offsets a difference in elevation between the first portion and the second portion of the side plate.

In still another embodiment, the shoe cover further includes a contact surface to receive a foot of a user of the walking assist device, and the first portion of the side plate is secured under the contact surface in the recessed portion.

In yet still another embodiment, the first portion is secured by means of bolts and threaded holes on the contact surface.

In still yet another embodiment, the first portion includes threaded holes in alignment with the threaded holes on the contact surface.

In a further embodiment, the second portion of the side plate is level with the contact surface while the first portion is secured in the recessed portion under the contact surface.

In another further embodiment, the first portion of the side plate is secured in a chamber defined by the shoe pad, the contact surface and the support plate.

Embodiments according to the present invention also provide a walking assist device. The walking assist device includes a shank stand, a side plate and a shoe assembly. The side plate, pivotably connected to the shank stand, includes a first portion and a second portion. The shoe assembly includes a shoe pad and a shoe cover. The shoe cover includes a recessed portion to accommodate the first portion of the side plate, and a support plate on the shoe pad to fulcrum the second portion of the side plate. The second portion covers the recessed portion while the first portion is held in the recessed portion.

The foregoing has outlined rather broadly the features and technical advantages of the present invention in order that the detailed description of the invention that follows may be better understood. Additional features and advantages of the invention will be described hereinafter, and form the subject of the claims of the invention. It should be appreciated by those skilled in the art that the conception and specific embodiment disclosed might be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

The objectives and advantages of the present invention will become apparent upon reading the following description and upon reference to the accompanying drawings in which.

DESCRIPTION OF THE EMBODIMENTS

The embodiments of the present invention are shown in the following description with the drawings, wherein similar or same components are indicated by similar reference numbers.

Figure 1A:
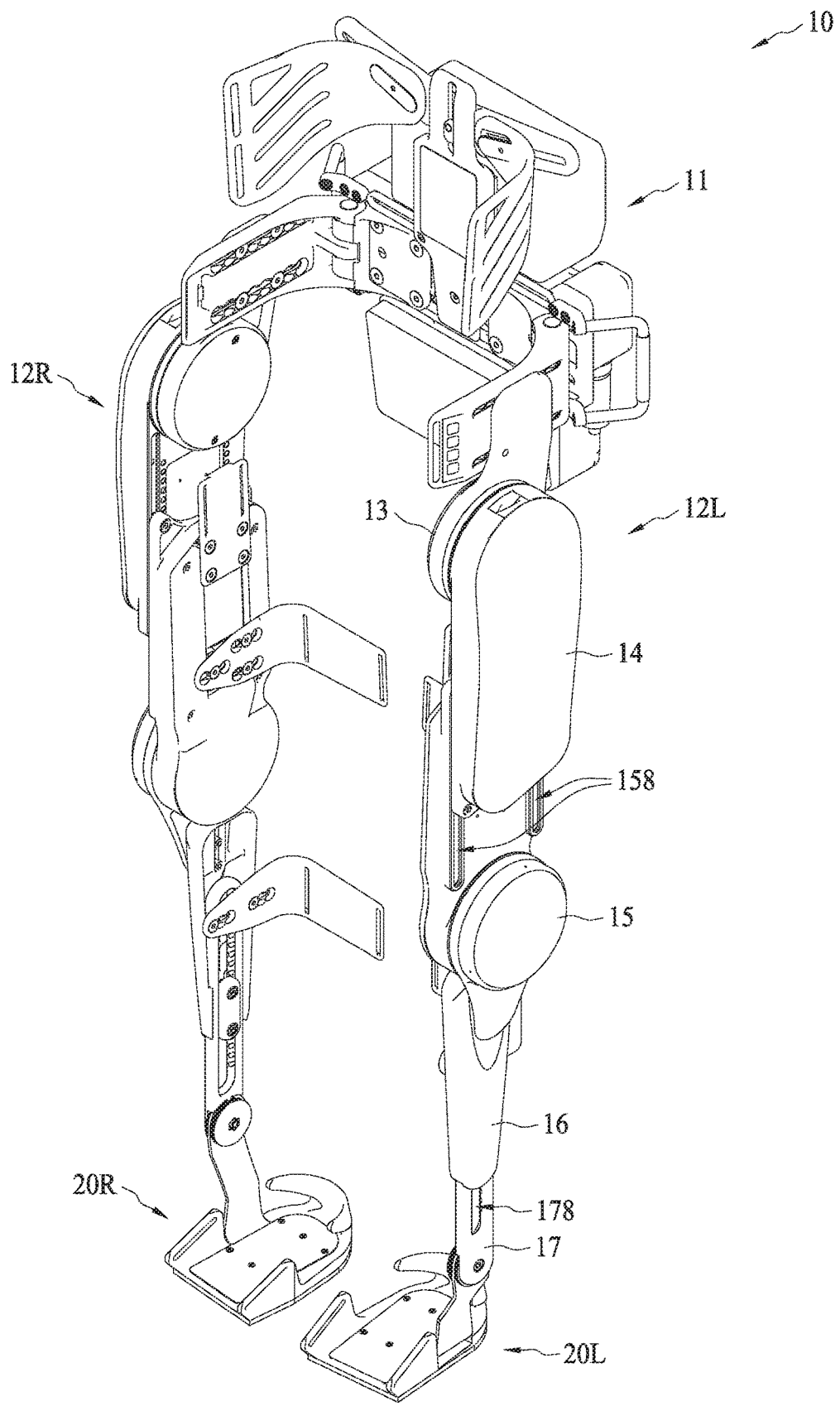
FIG. 1A is a perspective view of a walking assist device, in accordance with some embodiments of the present invention.
Figure 1B:
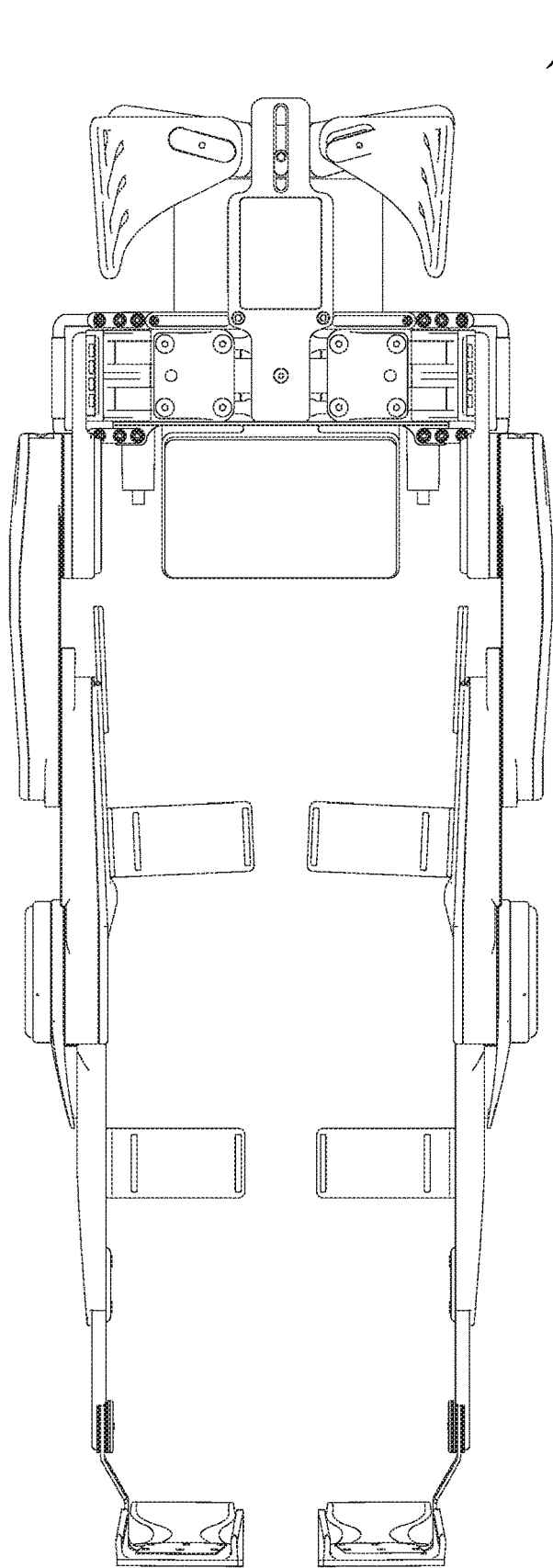
FIGS. 1B, 1C and 1D are a front view, right side view and top view of the walking assist device illustrated in FIG. 1A, respectively.
Figure 1C:
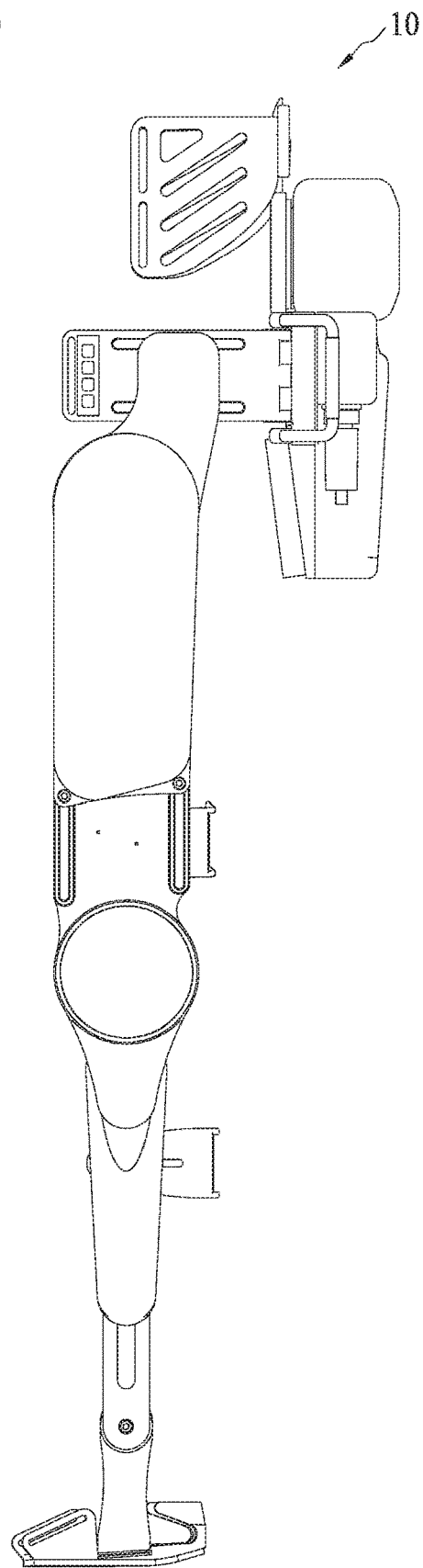
Figure 1D:
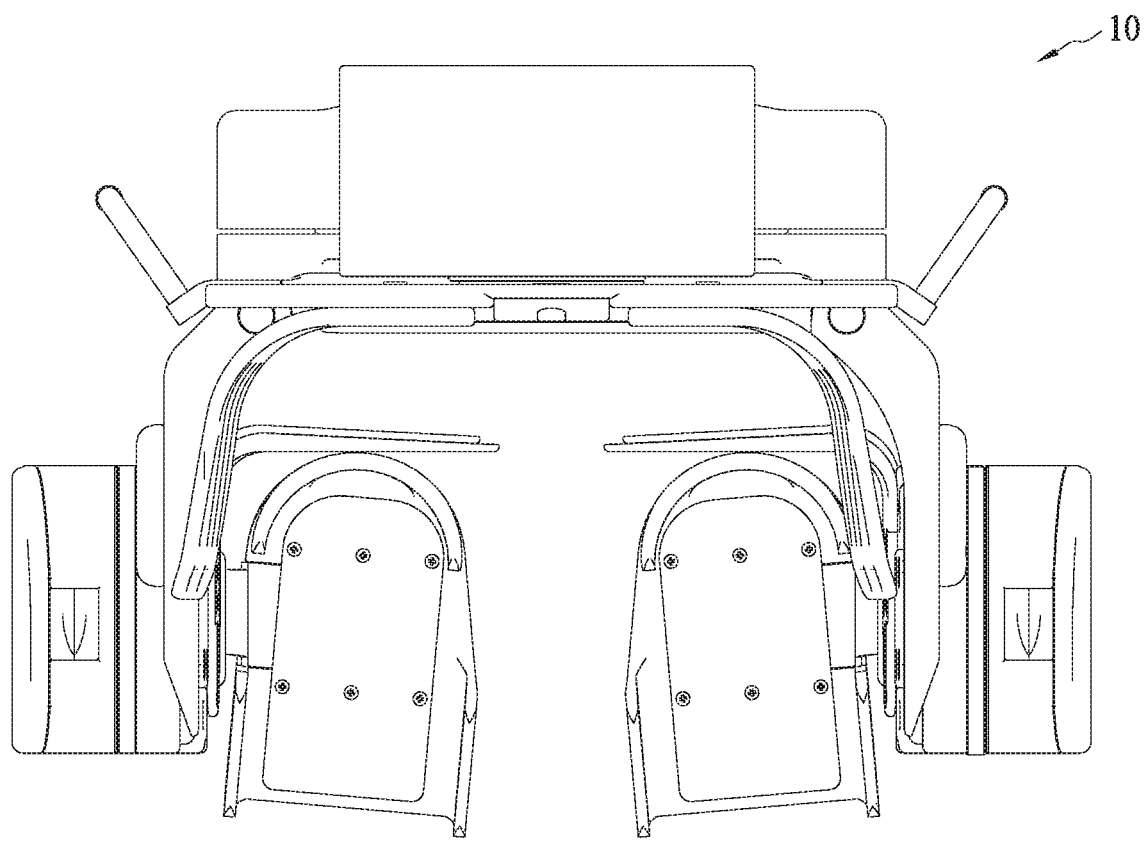

FIG. 1A is a perspective view of a walking assist device 10, while FIGS. 1B, 1C and 1D are a front view, right side view and top view of the walking assist device 10, respectively, in accordance with some embodiments. Referring to FIG. 1A, the walking assist device 10 includes a waist assembly 11, a right leg assembly 12R, a left leg assembly 12L, a right shoe assembly 20R and a left shoe assembly 20L.

The waist assembly 11 is configured to support a user of the walking assist device 10 at the waist. Each of the right leg assembly 12R and the left leg assembly 12L is pivotably connected to the waist assembly 11 via a respective hip joint 13. As a result, the right leg assembly 12R and the left leg assembly 12L are rotatable with respect to the waist assembly 11. Since the right leg assembly 12R and the left leg assembly 12L are symmetric in physical configuration to each other, for convenience, only the left leg assembly 12L is discussed.

The left leg assembly 12L includes a thigh stand 14, a shank stand 16, a knee joint 15 and an ankle joint 17 in addition to the hip joint 13. The thigh stand 14, having an elongated shape, is pivotably connected at one side (not numbered) to the waist assembly 11 via the hip joint 13, and pivotably connected at another side (not numbered) to the shank stand 16 via the knee joint 15. As a result, the thigh stand 14 and the shank stand 16 are rotatable with respect to the knee joint 15. Moreover, the thigh stand 14 is movable along a first adjusting means 158 of the knee joint 15 in the elongated direction so that the length of the left leg assembly 12L at the thigh portion is adjustable to suit the user's need. In the present embodiment, the first adjusting means 158 includes a pair of slots stretched in the elongated direction. In other embodiments, the first adjusting means 158 may include grooves, rails or sliding rods that facilitate the adjustment lengthwise.

The shank stand 16, also having an elongated shape, is pivotably connected at one side (not numbered) to the thigh stand 14 via the knee joint 15, and pivotably connected at another side (not numbered) to the shoe assembly 20 via the ankle joint 17. As a result, the shank stand 16 and the left shoe assembly 20L are rotatable with respect to the ankle joint 17. Moreover, the shank stand 14 is movable along a second adjusting means 178 of the ankle joint 17 in the elongated direction so that the length of the left leg assembly 12L at the shank portion is adjustable to suit the user's need. In the present embodiment, the second adjusting means 178 includes a slot stretched in the elongated direction. Alternatively, the second adjusting means 178 may include grooves, rails or sliding rods that facilitate the adjustment lengthwise.

The thigh stand 14, shank stand 16, hip joint 13, knee joint 15 and ankle joint 17 are similar to those disclosed in the U.S. application Ser. No. 14/519,145 (herein after the '145 application), entitled "Walking Assist Device," filed 21 Oct. 2014 by the same inventors of the subject application, and therefor are not described in detail. For more information on the physical relationship among and the functions of the thigh stand 14, shank stand 16, hip joint 13, knee joint 15 and ankle joint 17, reference can be made to the disclosure of the '145 application.

Figure 2A:
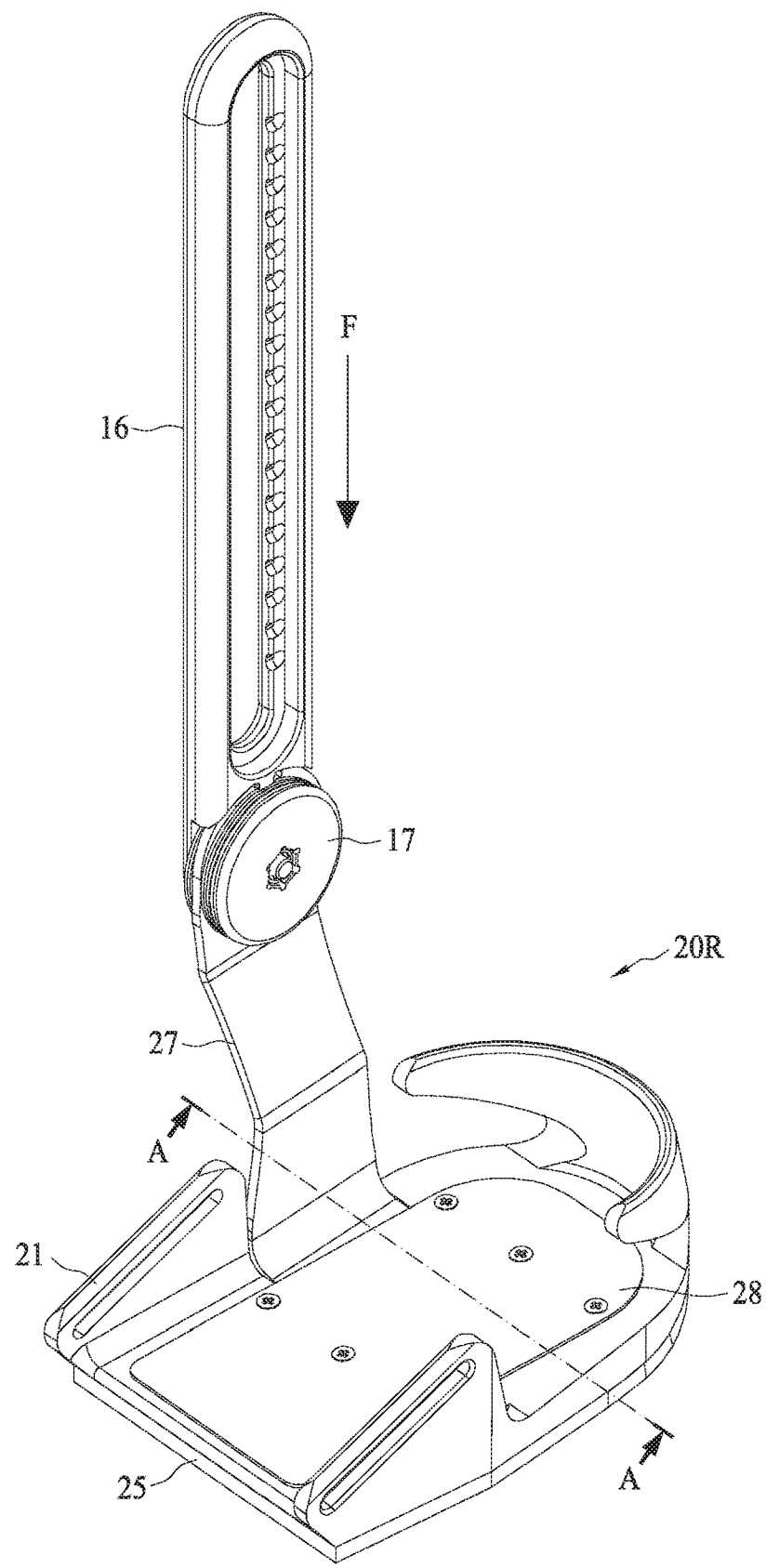
FIG. 2A is a perspective view of a shoe assembly of the walking assist device illustrated in FIG. 1A, in accordance with an embodiment of the present invention.
Figure 2B:
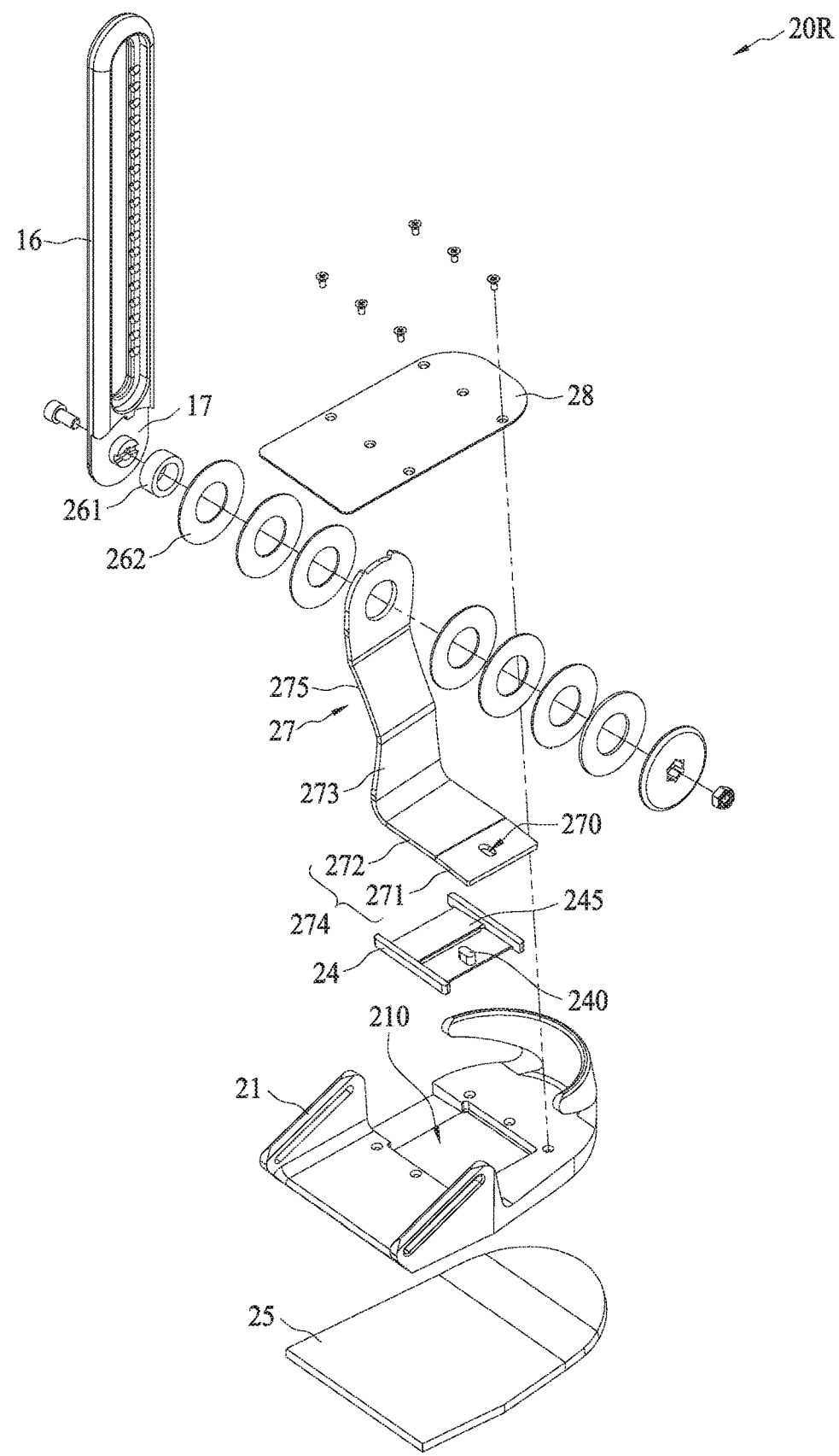
FIGS. 2B, 2C and 2D are an exploded view, a front view and a right side view of the shoe assembly illustrated in FIG. 2A, respectively.
Figure 2C:
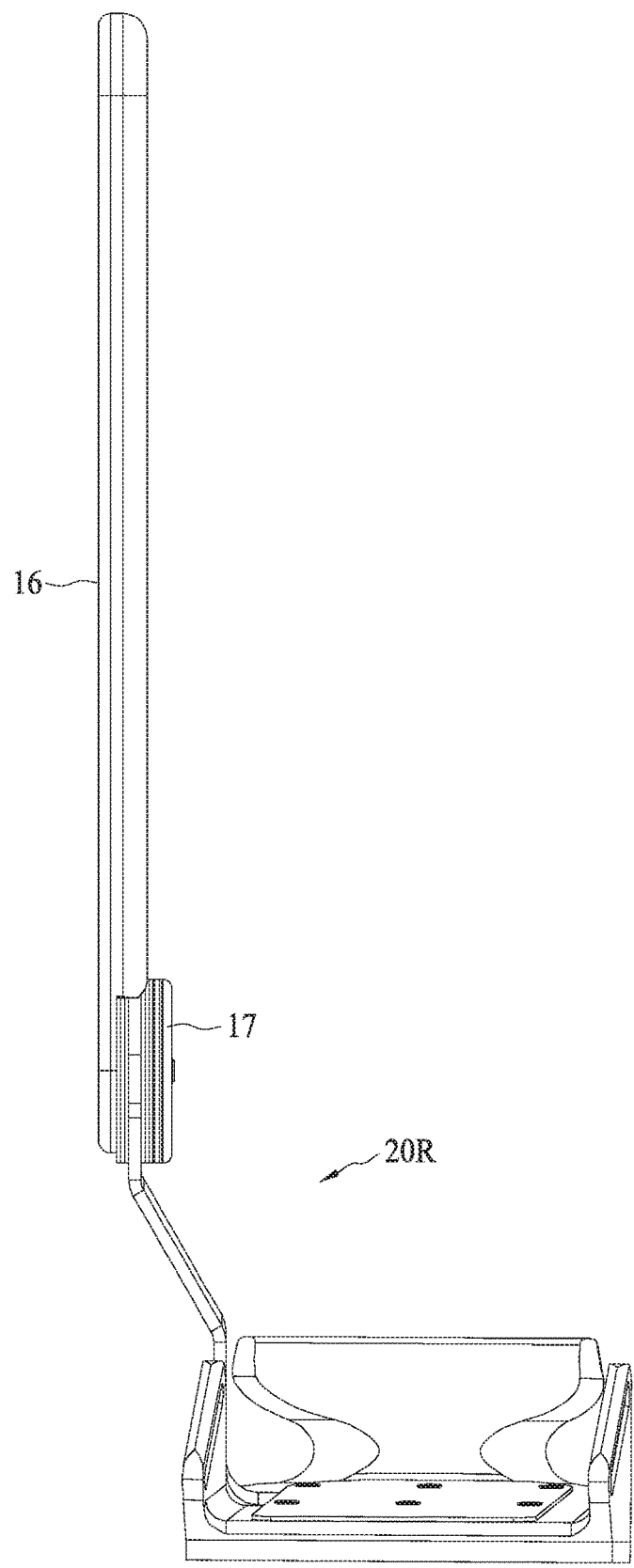
Figure 2D:
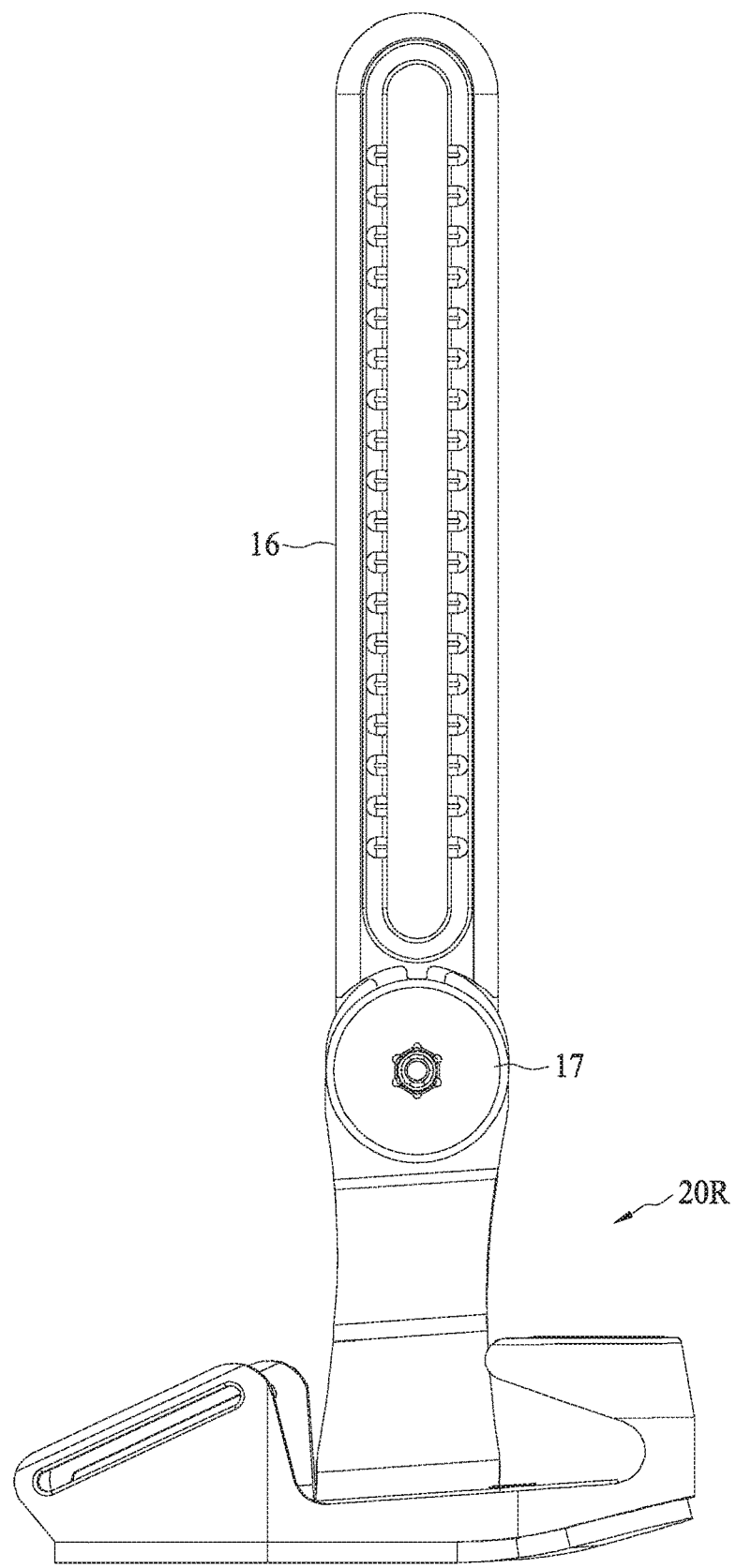

FIG. 2A is a perspective view of the right shoe assembly 20R together with its corresponding ankle joint 17, while FIGS. 2B, 2C and 2D are an exploded view, a front view and a right side view of the right shoe assembly 20R together with the ankle joint 17, respectively, in accordance with some embodiments. Likewise, since the right shoe assembly 20R and the left shoe assembly 20L are symmetric to each other, for convenience, only the right shoe assembly 20R is discussed in detail.

Referring to FIG. 2A, the right shoe assembly 20R includes a shoe cover 21, a shoe pad 25, a side plate 27 and a fix plate 28. The shoe cover 21 serves as a main body of the shoe assembly 20R to accommodate a user's foot or shoe. The shoe pad 25 serves as a sole for the shoe cover 21. In an embodiment, the shoe pad 25 is made of a material that provides an anti-slip function. The side plate 27, connected between the ankle joint 17 and the shoe cover 21, is configured to transmit a force F exerted through the shank stand 16 or ankle joint 17 in a first direction towards the shoe pad 25. The fix plate 28 facilitates to secure the side plate 27 to the shoe cover 21, and provides a smooth contact for the user's foot or shoe.

Referring to FIG. 2B, the right shoe assembly 20R further includes a support plate 24, which is hidden from the fix plate 28 in FIG. 2A. The support plate 24 is held in a recessed portion 210 of the shoe cover 21. In addition, the support plate 24 includes a male part 240 and a ridge 245, which will be further discussed in detail.

The side plate 27, formed in an integral piece, includes a first part 274, a second part 275, and a third part 273 connecting the first part 274 and the second part 275. The first part 274 further includes a first portion 271 and a second portion 272. The first portion 271 and the second portion 272 substantially extend in a second direction different from the first direction. In an embodiment, the first direction and the second direction are orthogonal to each other. The first portion 271 and the second portion 272 are also held in the recessed portion 210 of the shoe cover 21. Specifically, during assembly, the support plate 24 is placed in the recessed portion 210, with the ridge 245 extending in a third direction that is substantially orthogonal to the first and the second directions. Subsequently, the first portion 271 is stacked on the support plate 24 by mating a female part 270 of the first portion 271 with the male part 240 of the support plate 24. The fix plate 28 then covers the support plate 24, the first portion 271 and the second portion 272 in the recessed portion 210. In an embodiment, the first portion 271 is sized and configured to snugly fit in the support plate 24 so that the female part 270 and the male part 240 are aligned with each other. The female part 270 and the male part 240 facilitate to secure the support plate 24 to the first portion 271 of the side plate 27 in a chamber defined by the recessed portion 210 and the fix plate 28.

The second part 275 of the side plate 27 is connected to the ankle joint 17 by fastening means (not numbered) that may include a ring 261, washers 262 and a set of nut and bolt (not numbered).

Figure 3A:
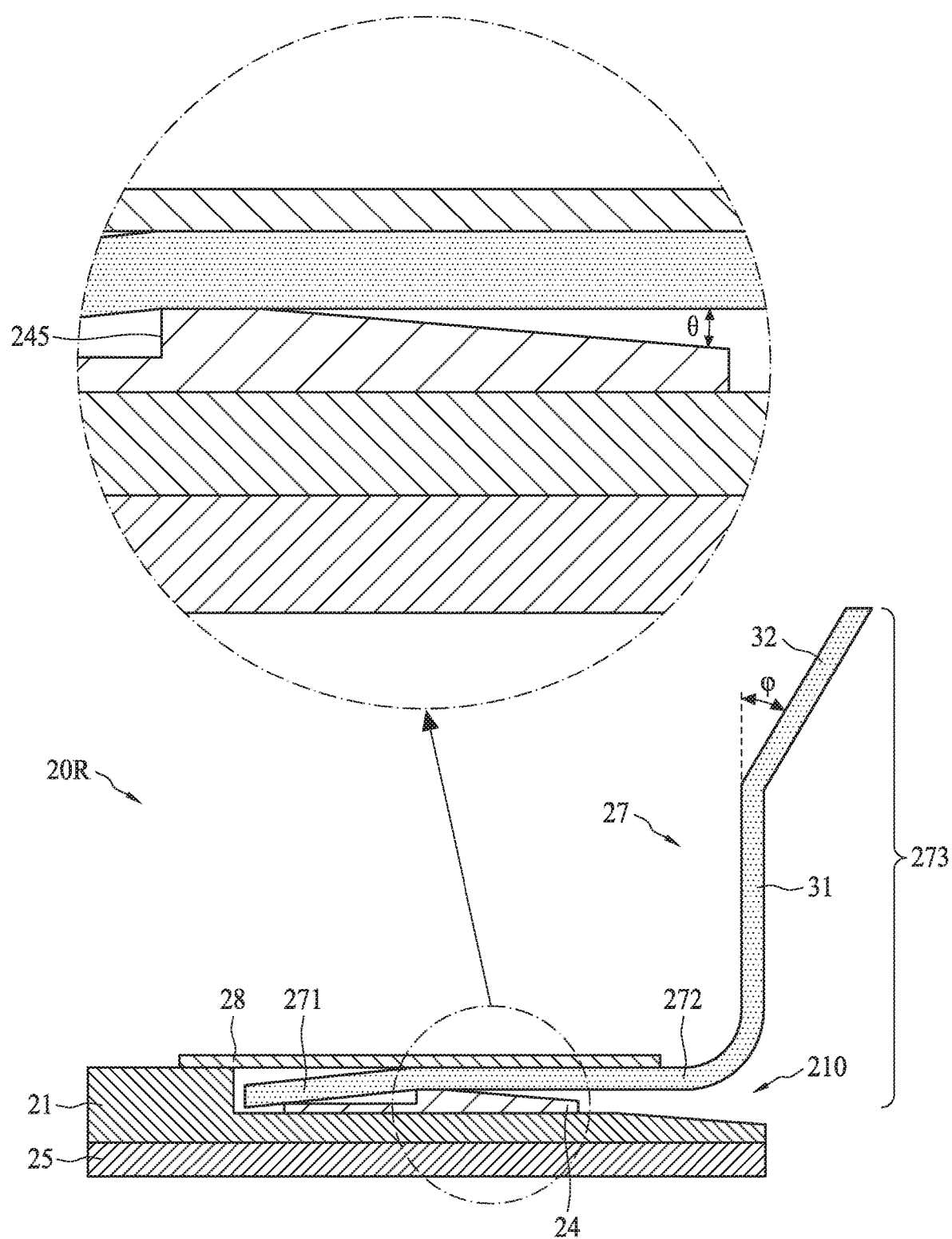
FIG. 3A is a cross-sectional view of the shoe assembly illustrated in FIG. 2A, taken from the AA direction, in accordance with some embodiments of the present invention.

FIG. 3A is a cross-sectional view of the right shoe assembly 20R described and illustrated with reference to FIG. 2A taken from the AA direction, in accordance with some embodiments.

Referring to FIG. 3A, in particular to an amplified view as illustrated, the ridge 245 of the support plate 24 is substantially located at a center line, extending in the third direction, of the support plate 24. The ridge 245 fulcrums the second portion 272 and tapers towards an opening of the recessed portion 210. The tapered surface forms a first angle θ with respect to the second portion 272. In an embodiment, the first angle θ ranges between approximately 1 degree and 5 degrees.

In addition, the third portion 273 of the side plate 27 may include a first section 31 that may extend in the elongated direction of the shank stand 16 or the thigh stand 14, and a second section 32 that may deflect outward from the elongated direction. The second section 32 forms a second angle Φ with respect to the first section 31. In an embodiment, the second angle Φ ranges between approximately 0 degree and 90 degrees.

Figure 3B:
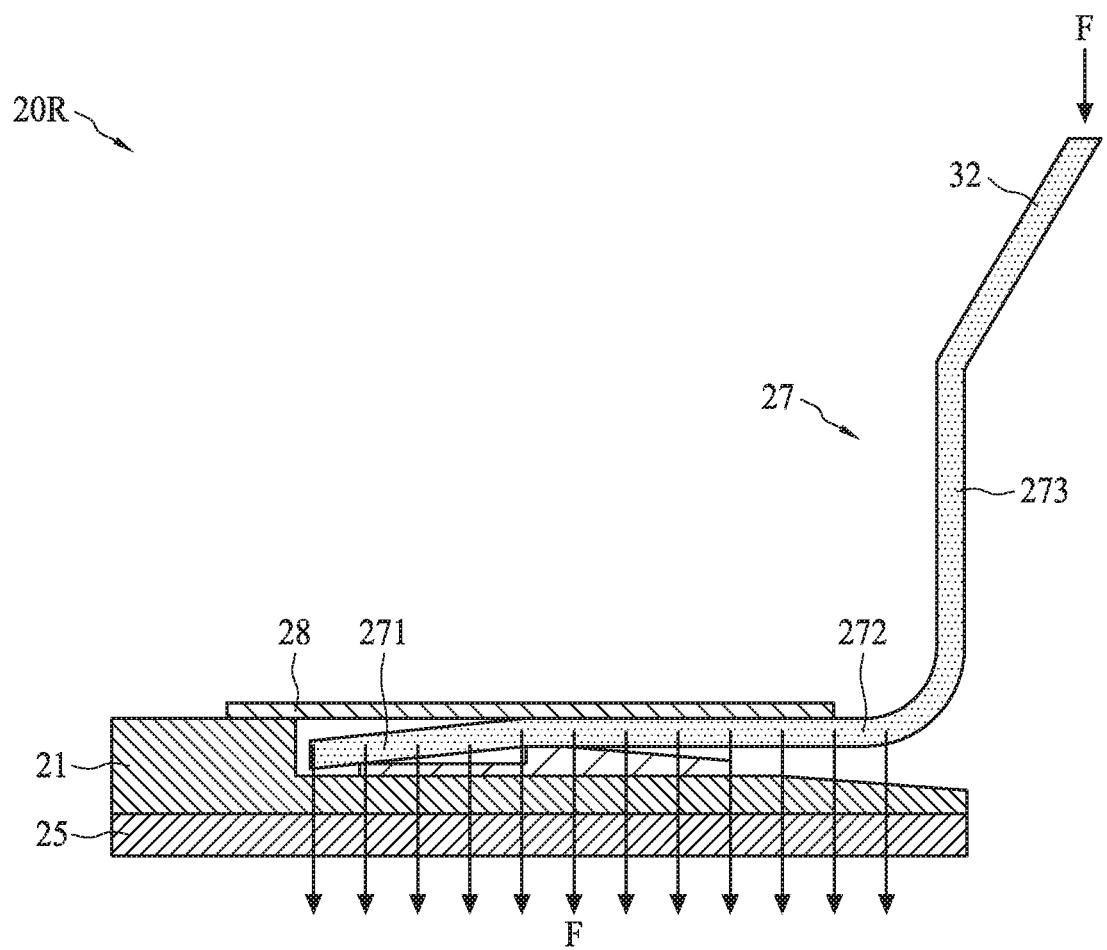
FIG. 3B is a schematic cross-sectional view showing a force transmission mechanism in the shoe assembly illustrated in FIG. 3A.

FIG. 3B is a schematic cross-sectional view showing a force transmission mechanism in the right shoe assembly 20R described and illustrated with reference to FIG. 3A.

Referring to FIG. 3B, a force F exerted via the shank stand 16, largely due to the weight of the user, is transmitted via the side plate 27 and the fix plate 28 towards the shoe cover 21 and the shoe pad 25. The ridge 245, which fulcrums the second portion 272, allows the second portion 272 to elastically deform in the recessed portion 210 within a range defined by the first angle θ. As a result, the force F is transmitted to the shoe pad 25 and uniformly distributed on the shoe pad 25.

In some existing walking assist devices, a gravitational force exerted via, for example, a shank stand to one side of a shoe is likely to cause the shoe to tilt or roll at the other side, which may danger the user. Moreover, a user of a walking assist device is generally a physically challenged person or a handicapped person with limited mobility. As compared to a normal person, such users, when put on an existing walking assist device, may tend to significantly sway to the right when the body of the user is supported with the right leg and sway to the left when the body of the user is supported with the left leg. The sway that would otherwise not occur for a normal person while walking produces an additional force exerted via, for example, a shank stand towards a shoe. The additional force would exacerbate the tilting problem. With the shoe assembly 20R according to the disclosure, the force is uniformly distributed over the shoe pad 25, which effectively ensures the shoe pad 25 to entirely contact a ground surface and thus prevents the shoe assembly 20R from the issue of tilting.

Figure 4:
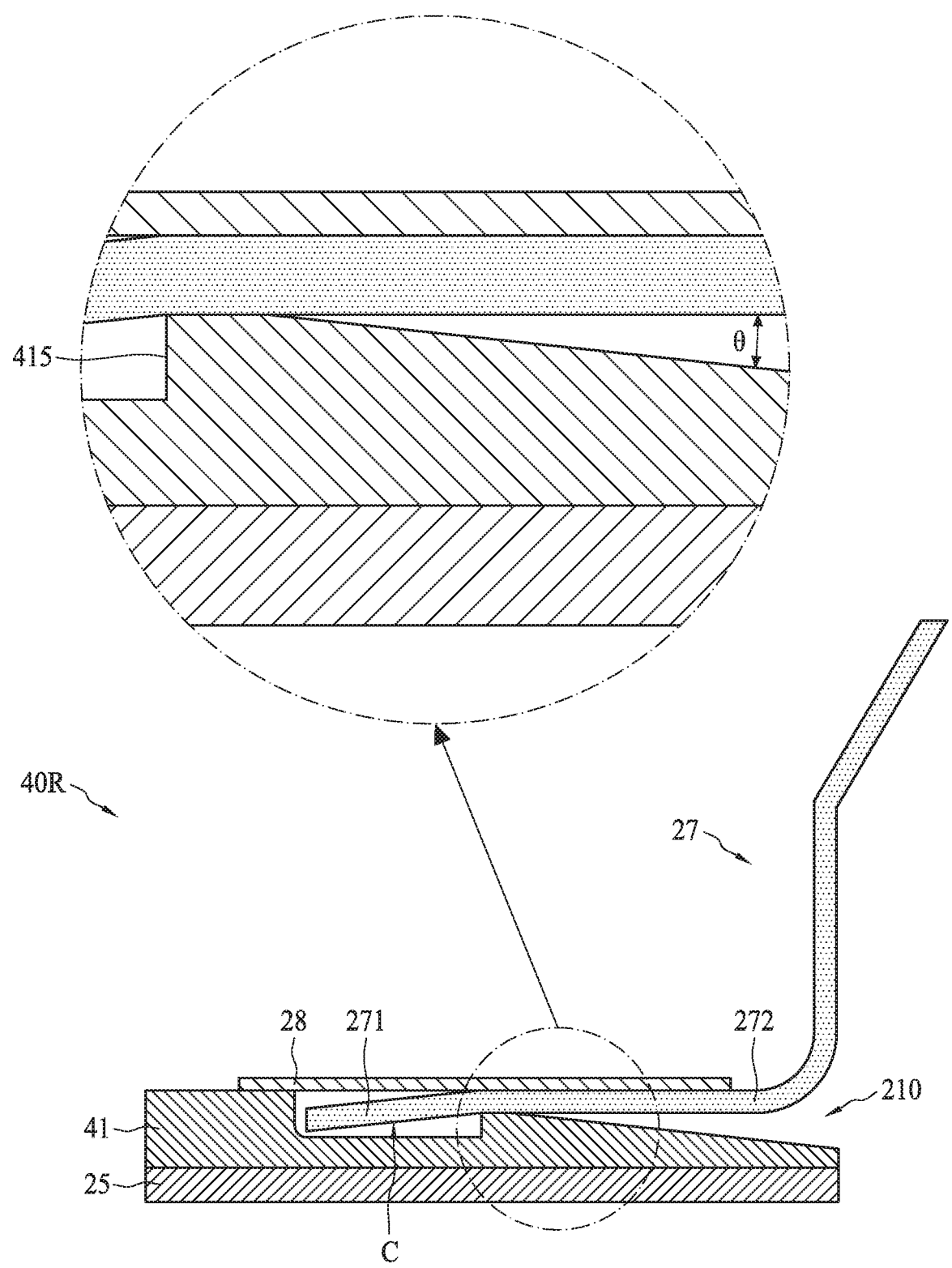
FIG. 4 is a perspective view of a shoe assembly of the walking assist device illustrated in FIG. 1A, in accordance with another embodiment of the present invention.

FIG. 4 is a perspective view of a shoe assembly 40R in accordance with another embodiment.

Referring to FIG. 4, the shoe assembly 40R is similar to the shoe assembly 20R described and illustrated with reference to FIG. 3A except that, for example, the shoe cover 21 and the support plate 24 of the shoe assembly 20R in FIG. 3A are integrated into a shoe cover 41 of the shoe assembly 40R. As illustrated in an amplified view, the shoe cover 41 includes a ridge 415 that fulcrums the second portion 272 of the side plate 27 in the recessed portion 210.

With the shoe assembly 40R, the force is uniformly distributed over the shoe pad 25, which effectively ensures the shoe pad 25 to entirely contact a ground surface and thus prevents the shoe assembly 40R from the issue of tilting.

Figure 5:
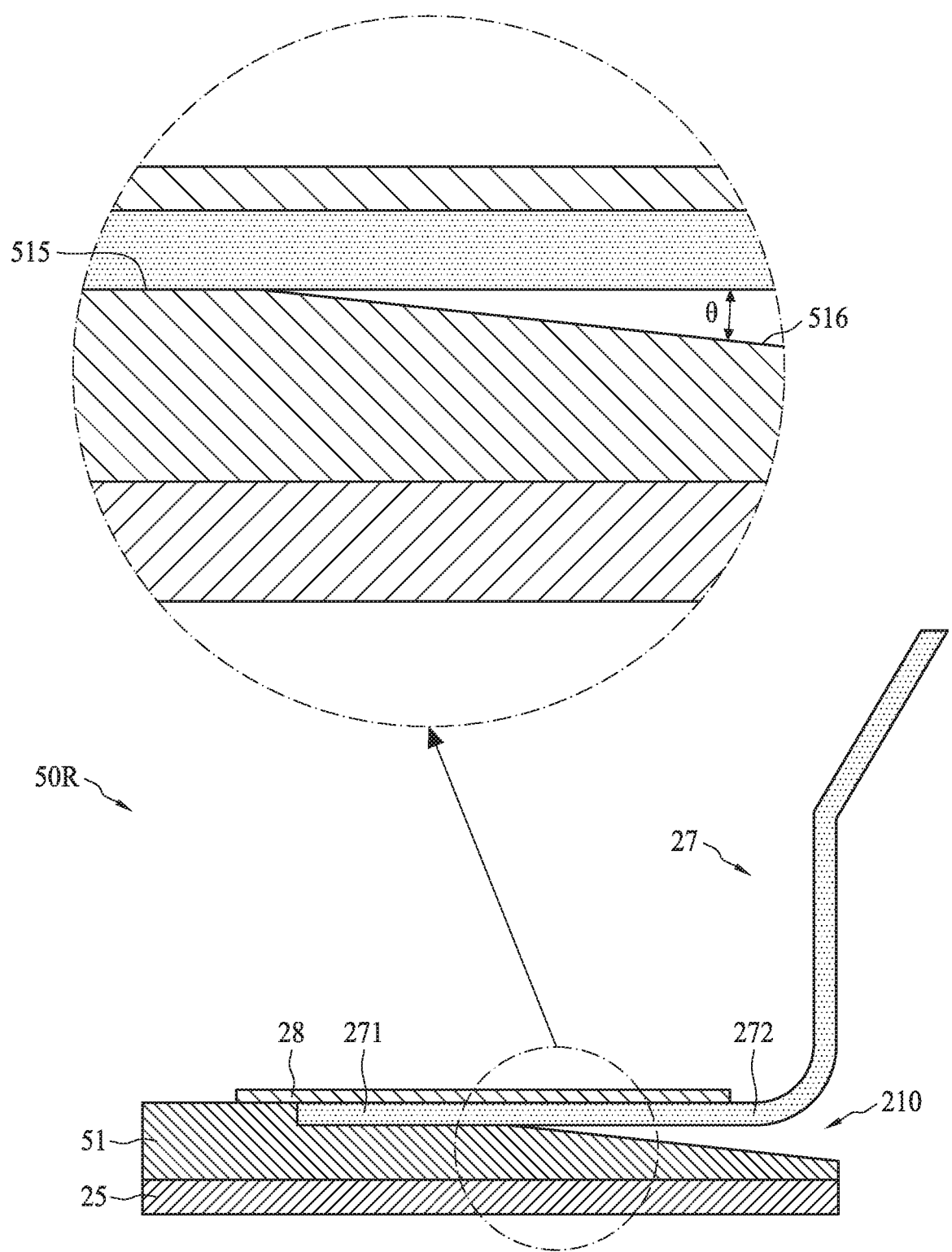
FIG. 5 is a perspective view of a shoe assembly of the walking assist device illustrated in FIG. 1A, in accordance with yet another embodiment of the present invention.

FIG. 5 is a perspective view of a shoe assembly 50R in accordance with another embodiment.

Referring to FIG. 5, the shoe assembly 50R is similar to the shoe assembly 20R described and illustrated with reference to FIG. 3A except that, for example, the shoe cover 21 and the support plate 24 of the shoe assembly 20R in FIG. 3A are integrated into a shoe cover 51 of the shoe assembly 50R. As illustrated in an amplified view, the shoe cover 51 includes a raised surface 515 and a slope 516 tapers from the raised surface 515. The raised surface 515 is configured to snugly accommodate the first portion 271 of the side plate 27 in a chamber C in the recessed portion 210. The slope 516 forms a first angle θ with respect to the second portion 272. The second portion 272 is allowed to elastically deform in the recessed portion 210 within a range defined by the first angle θ in response to a force.

With the shoe assembly 50R, the force is uniformly distributed over the shoe pad 25, which effectively ensures the shoe pad 25 to entirely contact a ground surface and thus prevents the shoe assembly 50R from the issue of tilting.

Figure 6A:
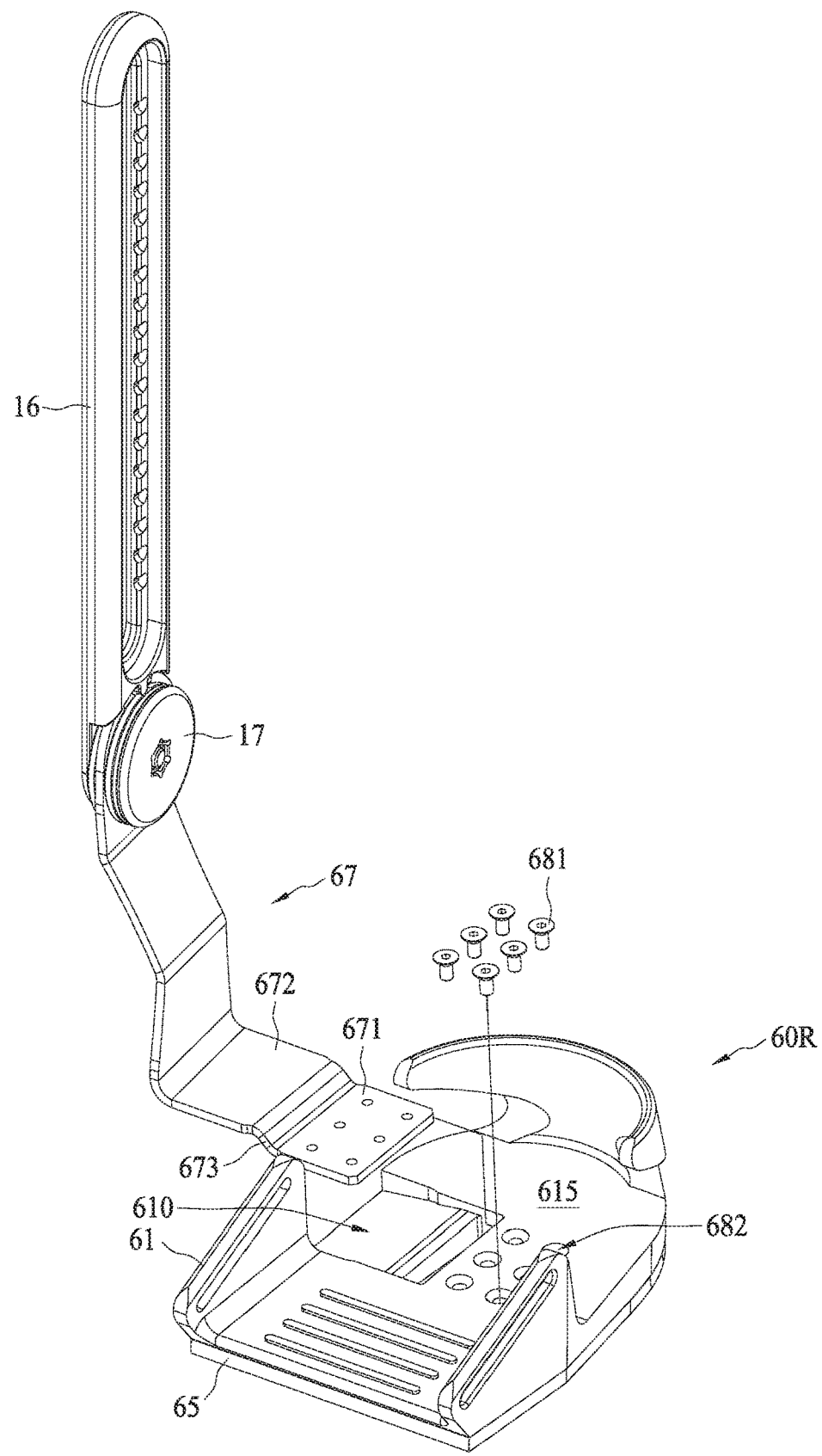
FIG. 6A is an exploded view of a shoe assembly of the walking assist device illustrated in FIG. 1A, in accordance with still another embodiment of the present invention.
Figure 6B:
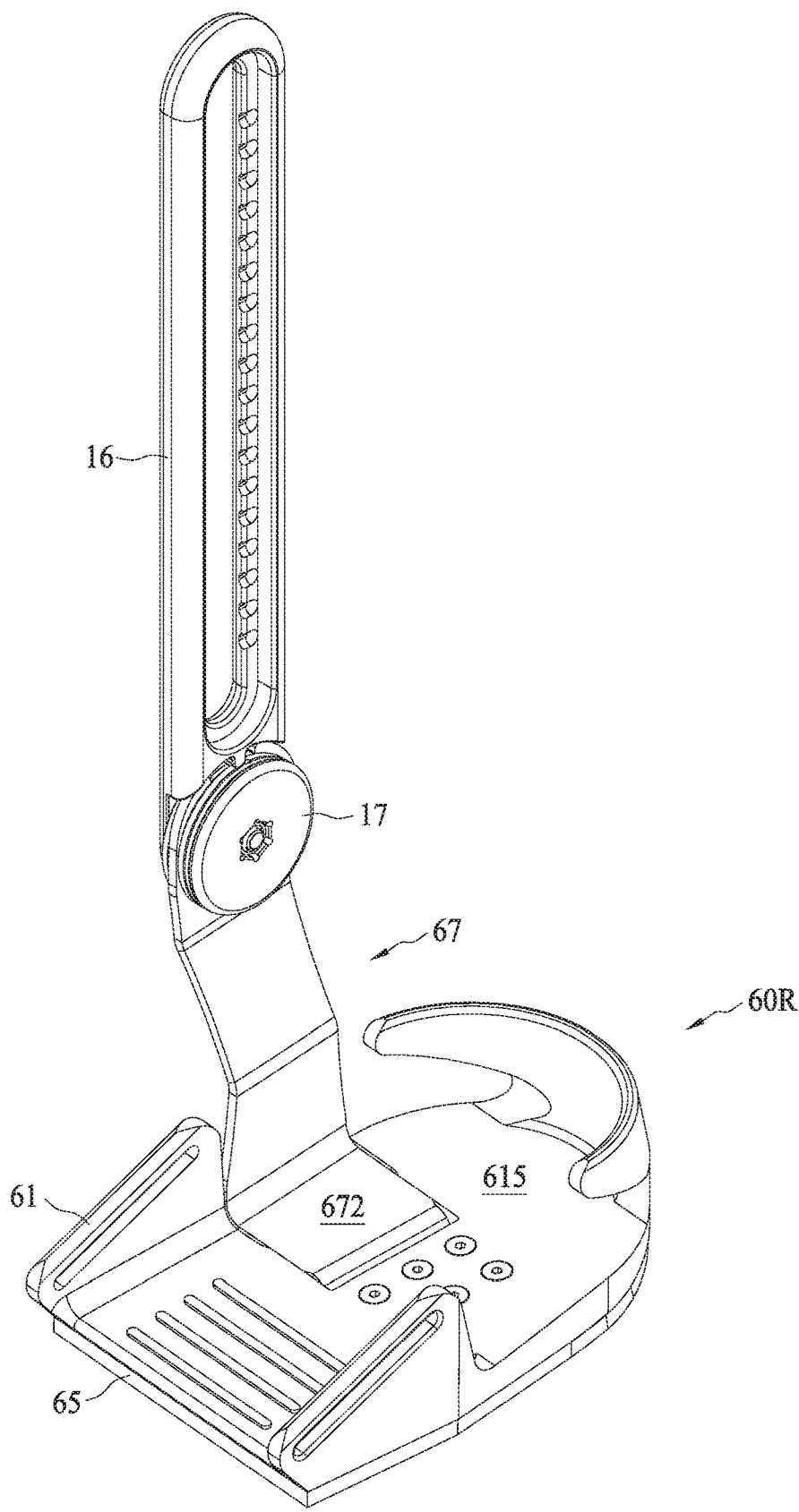
FIG. 6B is a perspective view of the shoe assembly illustrated in FIG. 6A when assembled.

FIG. 6A is an exploded view of a shoe assembly 60R of the walking assist device 10 illustrated in FIG. 1A, in accordance with still another embodiment of the present invention. FIG. 6B is a perspective view of the shoe assembly 60R illustrated in FIG. 6A when assembled.

Referring to FIG. 6A, the shoe assembly 60R includes a shoe cover 61 and a shoe pad 65. The shoe cover 61 serves as a main body of the shoe assembly 60R to accommodate a user's foot or shoe. The shoe pad 65 serves as a sole for the shoe cover 61. The shoe cover 21 includes a recessed portion 610 to accommodate a first portion 671 of a side plate 67 connected between the shoe cover 61 and the shank stand 16 of the walking assist device 10. Also, the shoe cover 21 includes a contact surface 615 to receive the user's foot or shoe. Also referring to FIG. 6B, the first portion 671 is to be held in the recessed portion 610 under the contact surface 615. Further, the second portion 672 covers the recessed portion 610 while the first portion 671 is held in the recessed portion 610. As shown in FIG. 6B, the second portion 672 of the side plate 67 is substantially level with the contact surface 615 while the first portion 671 is held in the recessed portion 610 under the contact surface 615.

Referring back to FIG. 6A, in the present embodiment, the first portion 671 is secured by means of bolts 681 and threaded holes 682 on the contact surface 615. Moreover, the first portion 671 includes threaded holes (not numbered) in alignment with the threaded holes 682 to facilitate securing the first portion 671 in the recessed portion 610.

The shank stand 16 extends in a first direction, and the first portion 671 and the second portion 672 of the side plate 67 extend in a second direction different from the first direction. In an embodiment, the second direction is substantially orthogonal to the first direction. The side plate 67 also includes a third portion 673 connecting the first portion 671 and the second portion 672 that extend in the second direction in different elevations. The difference in elevation between the first portion 671 and the second portion 672 facilitates a fulcrum operation, as will be further discussed with reference to FIG. 6D.

Figure 6C:
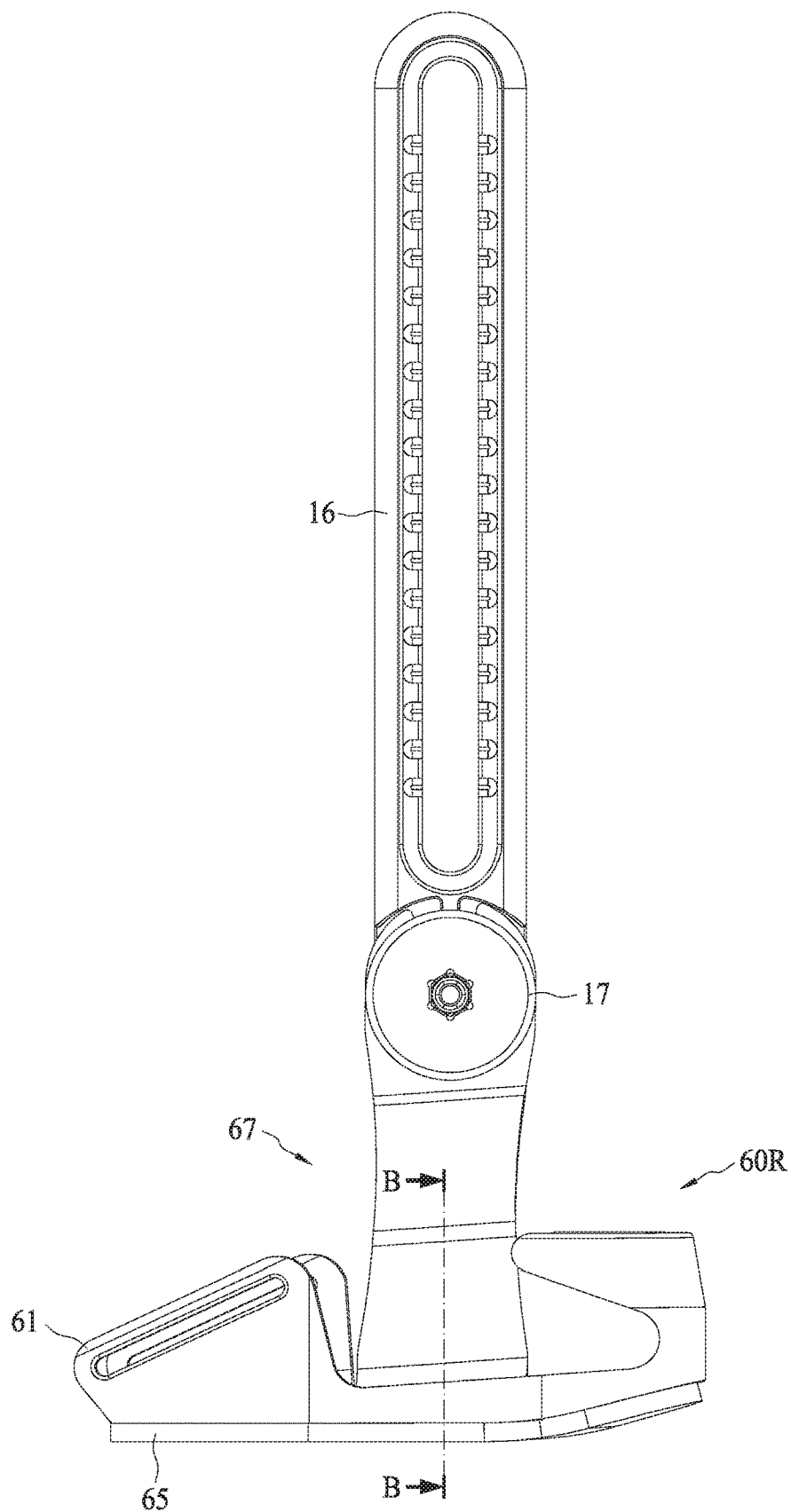
FIG. 6C is a right side view of the shoe assembly illustrated in FIG. 6A.
Figure 6D:
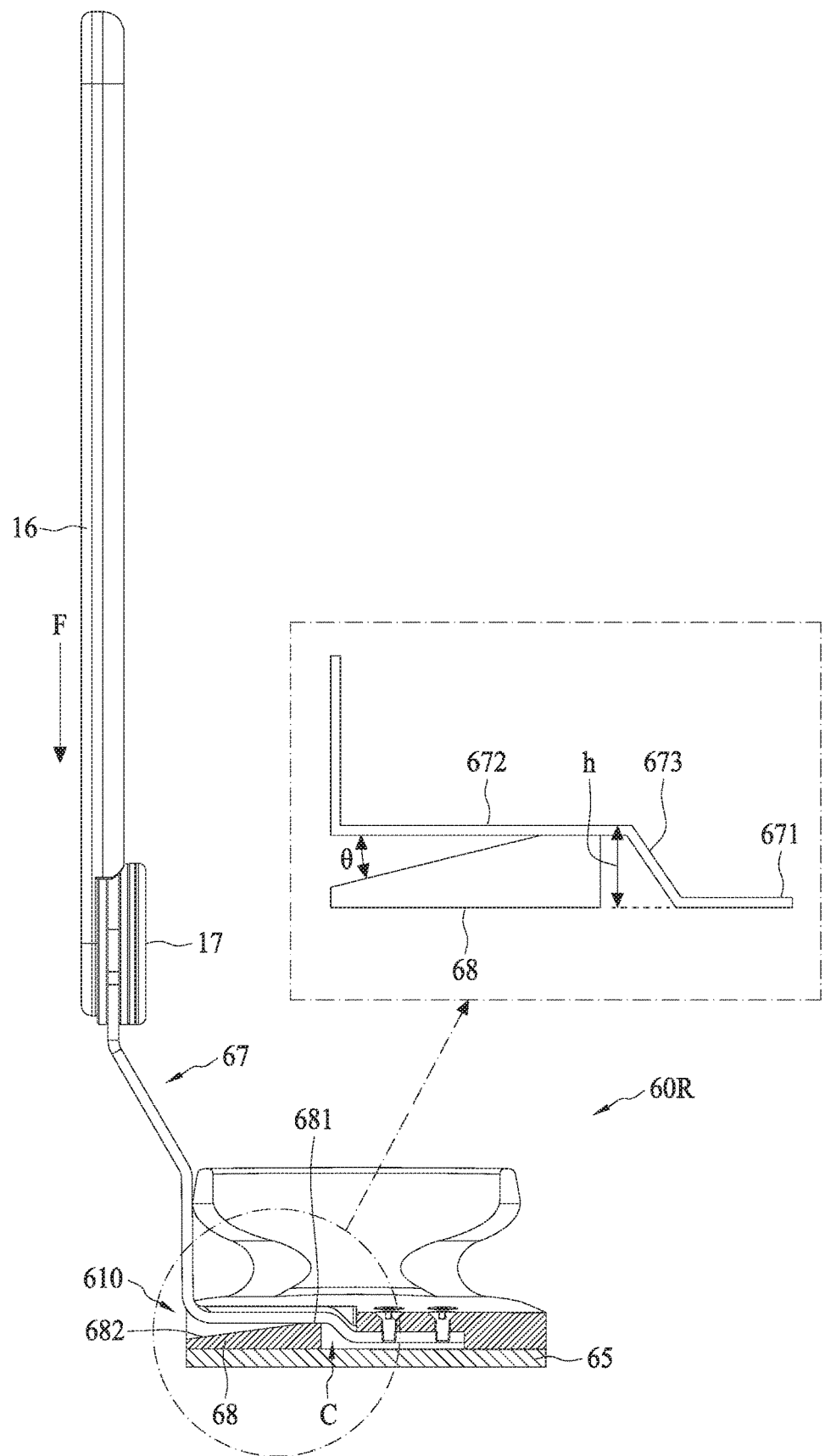
FIG. 6D is a cross-sectional view of the shoe assembly illustrated in FIG. 6C, taken from the BB direction, in accordance with some embodiments of the present invention.

FIG. 6C is a right side view of the shoe assembly 60R illustrated in FIG. 6A, and FIG. 6D is a cross-sectional view of the shoe assembly 60R illustrated in FIG. 6C, taken from the BB direction.

Referring to FIG. 6D, the shoe cover 21 includes a support plate 68 on the shoe pad 65 to fulcrum the second portion 672 of the side plate 67. The first portion 671 of the side plate 67 is secured in a chamber C defined by the shoe pad 65, the contact surface 615 and the support plate 68.

In operation, the second portion 672 is elastically deformed in response to a force F exerted along the first direction. The support plate 68 includes a raised surface 681 to fulcrum the second portion 672, and a slope 682 having an inclined surface to rest the second portion 672 when elastically deformed.

In an amplified view as illustrated, the second portion 672 is disposed at a higher elevation than the first portion 671. The elevation difference facilitates the first portion 671 to stretch into the chamber C for a better securing effect, and allows the second portion 672 fulcrumed on the raised surface 681 to elastically deform in response to the force F. In an embodiment, the support plate 68 has a height h substantially equals the elevation difference.

Although the present invention and its advantages have been described in detail, it should be understood that various changes, substitutions and alterations can be made herein without departing from the spirit and scope of the invention as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A shoe assembly for a walking assist device, the shoe assembly comprising:
   a shoe pad;
   a shoe cover comprising a recessed portion;
   a side plate connected between the shoe cover and a shank stand of the walking assist device, and including a first portion and a second portion held in the recessed portion; and
   a support plate in the recessed portion to fulcrum the second portion of the side plate while the first portion is held in the recessed portion.

2. The shoe assembly according to claim 1, wherein the shank stand extends in a first direction, and the first portion and the second portion of the side plate extend in a second direction different from the first direction.

3. The shoe assembly according to claim 2, wherein the second portion is elastically deformed in response to a force exerted along the first direction.

4. The shoe assembly according to claim 3, wherein the support plate includes a raised surface to fulcrum the second portion, and a slope having an inclined surface to receive the second portion when elastically deformed.

5. The shoe assembly according to claim 1, wherein the support plate having a height that offsets a difference in elevation between the first portion and the second portion of the side plate.

6. The shoe assembly according to claim 1, wherein the shoe cover further comprises a contact surface to receive a foot of a user of the walking assist device, and the first portion of the side plate is secured under the contact surface in the recessed portion.

7. The shoe assembly according to claim 6, wherein the first portion is secured by means of bolts and threaded holes on the contact surface.

8. The shoe assembly according to claim 7, wherein the first portion includes threaded holes in alignment with the threaded holes on the contact surface.

9. The shoe assembly according to claim 6, wherein the second portion of the side plate is level with the contact surface while the first portion is secured in the recessed portion under the contact surface.

10. The shoe assembly according to claim 6, wherein the first portion of the side plate is secured in a chamber defined by the shoe pad, the contact surface and the support plate.

11. The shoe assembly according to claim 1, wherein the side plate is pivotably connected to the shank stand.

12. The shoe assembly according to claim 11, wherein the shank stand extends in a first direction, and the first portion and the second portion of the side plate extend in a second direction orthogonal to the first direction.

13. The shoe assembly according to claim 12, wherein the second portion is elastically deformed in response to a force exerted along the first direction.

14. The shoe assembly according to claim 13, wherein the support plate includes a raised surface to fulcrum the second portion, and a slope having an inclined surface to receive the second portion when elastically deformed.

15. The shoe assembly according to claim 11, wherein the support plate having a height that offsets a difference in elevation between the first portion and the second portion of the side plate.

16. The shoe assembly according to claim 11, wherein the shoe cover further comprises a contact surface to receive a foot of a user of the walking assist device, and the first portion of the side plate is secured under the contact surface in the recessed portion.

17. The shoe assembly according to claim 16, wherein the first portion is secured by means of bolts and threaded holes on the contact surface.

18. The shoe assembly according to claim 17, wherein the first portion includes threaded holes in alignment with the threaded holes on the contact surface.

19. The shoe assembly according to claim 16, wherein the second portion of the side plate is level with the contact surface while the first portion is secured in the recessed portion under the contact surface.

20. The shoe assembly according to claim 16, wherein the first portion of the side plate is secured in a chamber defined by the shoe pad, the contact surface and the support plate.

* * * * *